(12) United States Patent
Toben et al.

(10) Patent No.: US 8,765,001 B2
(45) Date of Patent: Jul. 1, 2014

(54) TEXTURING OF MONOCRYSTALLINE SEMICONDUCTOR SUBSTRATES TO REDUCE INCIDENT LIGHT REFLECTANCE

(75) Inventors: Michael P. Toben, Smithtown, NY (US); Robert K. Barr, Shrewsbury, MA (US); Corey O'Connor, Worcester, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 0 days.

(21) Appl. No.: 13/597,244

(22) Filed: Aug. 28, 2012

(65) Prior Publication Data

US 2014/0065836 A1 Mar. 6, 2014

(51) Int. Cl.
*B44C 1/22* (2006.01)

(52) U.S. Cl.
USPC .......... 216/99; 216/83; 216/96; 438/71; 438/689; 438/745; 438/752; 438/753; 257/E21.214; 257/E21.223; 136/256

(58) Field of Classification Search
None
See application file for complete search history.

(56) References Cited

U.S. PATENT DOCUMENTS

| 7,955,989 B2 | 6/2011 | Barr et al. |
| 2005/0247674 A1 | 11/2005 | Kubelbeck et al. |
| 2011/0081742 A1* | 4/2011 | Barr et al. ............... 438/71 |

FOREIGN PATENT DOCUMENTS

| JP | 11107000 A | 4/1999 | |
| JP | 2004212858 A | 7/2004 | |
| JP | 2005331913 A | 12/2005 | |
| WO | WO 2011/052941 A3 | 5/2011 | |
| WO | WO2011052941 | * 5/2011 | ............. C09K 13/02 |

OTHER PUBLICATIONS

Linde et al.; "Catalytic control of anisotropic silicon etching", Sensors and Actuators A, 1995; vol. 49; pp. 181-185.
European Search Report of corresponding European Application No. 13181957.5; Search Report dated Mar. 14, 2014.

* cited by examiner

*Primary Examiner* — Lan Vinh
*Assistant Examiner* — Jiong-Ping Lu
(74) *Attorney, Agent, or Firm* — John J. Piskorski (57) ABSTRACT

Monocrystalline semiconductor substrates are textured with alkaline solutions to form pyramid structures on their surfaces to reduce incident light reflectance and improve light absorption of the wafers. The alkaline baths include hydantoin compounds and derivatives thereof in combination with alkoxylated glycols to inhibit the formation of flat areas between pyramid structures to improve the light absorption.

4 Claims, 2 Drawing Sheets

TEXTURING OF MONOCRYSTALLINE SEMICONDUCTOR SUBSTRATES TO REDUCE INCIDENT LIGHT REFLECTANCE

FIELD OF THE INVENTION

The present invention is directed to a method of texturing monocrystalline semiconductor substrates in alkaline baths to reduce incident light reflectance. More specifically, the present invention is directed to a method of texturing monocrystalline semiconductor substrates in alkaline baths which include hydantoin or hydantoin derivatives in combination with alkoxylated glycols to reduce incident light reflectance.

BACKGROUND OF THE INVENTION

A textured semiconductor surface reduces reflection across wide bands of incident light thereby increasing absorbed light intensity. Such semiconductors may be used in the manufacture of solar cells. Solar cells are devices that convert light energy incident on their surfaces such as sunlight into electric energy. Reducing the reflectance of light incident on the surface improves conversion efficiency into electric energy. Texturing, however, is not restricted to semiconductors in the manufacture of solar cells but also may be used in the manufacture of photovoltaic devices in general, optical and electrochemical detectors/sensors, biodetectors/biosensors, catalysts, electrodes, and other devices where reducing the reflectance of incident light improves the efficiency of the device.

Known techniques for wet chemical pyramidal (tetragonal) structure texturing of (100)-orientated silicon surfaces use alkaline media, such as solutions of alkali hydroxides, alkali carbonates, ammonia or choline. Alkali hydroxides by themselves produce unevenly textured surfaces which result in areas of high reflectivity. An additive is typically included to control the texturing rate and to form repeatable pyramid structures. Solutions of hydrazine or ethylene diamine or pyrocatechol can be used instead of alkali hydroxides but they are disadvantageous on account of their toxicity to workers. The most common formulations include water, sodium or potassium hydroxide and alcohol. The alcohol component may be used to control the etch rate of the alkali hydroxides. The alcohol component used is either ethylene glycol or isopropanol. Although isopropanol is included in many conventional texturing compositions, its low boiling point and low flash point are undesirable properties for texturing compositions.

WO 2011/052941 discloses examples of alkaline etching compositions which exclude isopropanol for texturing crystalline silicon based wafers to form pyramid structures. The etching compositions include at least one alkaline compound, at least one cyclic compound having a boiling point of 100-400° C. and the balance of the formulation is water. The cyclic compounds are included to inhibit over etching of the silicon by the alkaline compounds. The cyclic compounds are $C_4$-$C_{10}$ heterocyclic compounds with one or more heterogeneous elements selected from nitrogen, oxygen and sulfur. The cyclic compounds are included in amounts of 0.1-50 wt % of the etching composition. Although there are alkaline texturing compositions which exclude isopropanol for the formation of pyramid structures on crystalline silicon wafers, there is still a need for an improved alkaline texturing composition and method for forming pyramid structures on crystalline silicon wafers.

SUMMARY OF THE INVENTION

Methods include providing a monocrystalline semiconductor substrate; providing a composition including one or more compounds chosen from hydantoin and hydantoin derivatives, one or more alkoxylated glycols and one or more alkaline compounds; and contacting the monocrystalline semiconductor substrate with the composition to anisotropically texture the monocrystalline semiconductor substrate.

Compositions include one or more compounds chosen from hydantoin and hydantoin derivatives, one or more alkoxylated glycols and one or more alkaline compounds.

The methods and compositions are used to anisotropically texture monocrystalline semiconductors for photovoltaic devices, including semiconductors in the manufacture of solar cells. The addition of one or more of hydantoin and hydantoin derivatives in combination with one or more alkoxylated glycols inhibit or reduce formation of flat areas between pyramid structures on the textured monocrystalline semiconductors to increase incident light absorption and improve the efficiency of the devices. In addition, the hydantoin compounds improve the efficiency of the texturing method.

DETAILED DESCRIPTION OF THE INVENTION

As used throughout this specification, the terms "depositing" and "plating" are used interchangeably. The terms "current tracks" and "current lines" are used interchangeably. The terms "solution", "bath" and "composition" are used interchangeably. The terms "texturing" and "etching" are used interchangeably. The indefinite articles "a" and "an" are intended to include both the singular and the plural. The term "selectively depositing" means that deposition occurs at specific desired areas on a substrate. The term "flash point" means the lowest temperature at which the vapor of a combustible liquid can be ignited in air. The unit "dynes" is a centimeter-grams-second unit of force.

The following abbreviations have the following meanings unless the context clearly indicates otherwise: ° C.=degrees Celsius; g=grams; L=liter; bv=by volume; A=amperes; m=meters; dm=decimeter; cm=centimeter; μm=microns; nm=nanometers; min.=minutes; ppm=part per million; ppb=parts per billion; SEM=scanning electron micrograph; UV=ultraviolet; and IR=infrared. All percentages and ratios are by weight unless otherwise indicated. All ranges are inclusive and combinable in any order except where it is logical that such numerical ranges are constrained to add up to 100%.

Compositions for texturing semiconductor substrates include one or more of hydantoin and hydantoin derivatives. Such hydantoin and hydantoin derivatives include, but are not limited to, compounds having a general formula:

(I)

where $R_1$, $R_2$, $R_3$ and $R_4$ may be the same or different and are hydrogen, $C_1$-$C_5$ alkyl, $C_1$-$C_4$ alkoxy, hydroxyl, $C_1$-$C_4$ alcohol or $C_5$-$C_6$ aryl, and $R_2$ or $R_3$ also may be —NH—C(O)NH$_2$, and X is oxygen or sulfur.

Examples of such compounds are hydantoin, 1-methylhydantoin, 1,3-dimethylhydantoin, 5,5-dimethylhydantoin, allantoin and 2-thiohydantoin. Preferably, the compounds are hydantoin, 5,5-dimethylhydantoin and 2-thiohydantoin.

In general, such hydantoin and hydantoin derivatives are solids at room temperature and higher. Preferably such compounds have melting points of 170° C. and greater. More preferably the melting points are 200° C. to 240° C. Typically such compounds decompose before becoming a liquid, thus they typically do not have boiling points.

The hydantoin and hydantoin derivatives are included in amounts of 0.001 wt % to 1 wt %, preferably 0.005 wt % to 0.5 wt %, more preferably 0.01 wt % to 0.1 wt %.

Solutions for texturing semiconductor substrates include one or more alkoxylated glycols. Such alkoxylated glycols have a weight average molecular weight of 100 g/mole and greater, such as, for example, dipropylene glycol, diethylene glycol and dipropylene glycol monomethyl ether. Preferably, the alkoxylated glycols have a weight average molecular weight of 170 g/mole or greater and a flash point of 75° C. or greater. More preferably, the weight average molecular weight of the alkoxylated glycols range from 170 g/mole to 4000 g/mole, most preferably from 190 g/mole to 500 g/mole. Flash points more preferably range from 75° C. to 300° C. or such as from 100° C. to 300° C. Most preferably, flash points range from 140° C. to 200° C. Alkoxylated glycols used in the texturing solutions are either water-soluble or at least water-miscible. The flash points of 75° C. or greater provide non-volatile texturing solutions preventing substantial evaporation of solution components. In addition, the preferred alkoxylated glycols have boiling points of 190° C. or greater which further reduces the amount lost at operating temperatures. Accordingly, the texturing solutions may be used over longer periods of time than many conventional texturing solutions. This reduces downtime for manufacturing processes and reduces the frequency of solution replacement, thus improving the overall efficiency of the texturing method. This improved efficiency of the method reduces costs to both consumers and manufactures alike.

Alkoxylated glycols are included in the solution in amounts of 0.001 wt % to 3 wt % of the solution. Preferably, the alkoxylated glycols are included in amounts of 0.1 wt % to 2 wt % of the solution. The alkoxylated glycols are non-cyclic but are linear or branched compounds. Alkoxylated glycols include, but are not limited to, compounds having a general formula:

$$HO(C_xH_{2x}O)_mH \quad (II)$$

wherein m is an integer of 2 or greater, or such as from 3 or greater, or such as from 8 to 66. Preferably, m is an integer of 3 to 6, more preferably from 3 to 5 and x is an integer of 3 to 6, or such as from 3 to 4. Examples of such alkoxylated glycols are dipropylene glycol, tripropylene glycol, tetrapropylene glycol, polypropylene glycol, tributylene glycol, tetrabutylene glycol, polybutylene glycol, tripentylene glycol, tetrapentylene glycol and polypentylene glycol.

Alkoxylated glycols also include, but are not limited to, compounds having a general formula:

$$HO(CH_2CH_2O)_nH \quad (III)$$

wherein n is an integer of 2 or greater, or such as 3 or greater, or such as from 5 to 200. Preferably, n is an integer of 3 to 5, more preferably from 3 to 4. Examples of such alkoxylated glycols are diethylene glycol, triethylene glycol, tetraethylene glycol and polyethylene glycol.

The combination of the hydantoin compounds and the alkoxylated glycols provide uniform texturing as well as reproducibility of pyramid structure formation on semiconductors. Flat areas on the surface of the wafer where pyramid structures are absent are reduced or eliminated. This results in reduced incident light reflectance and improved conversion efficiency of incident light into electric energy. In addition, the hydantoin compounds allow for the effected start-up of the texturing solution to further improve the efficiency of the texturing method. Effected start-up refers to new or fresh texturing solutions for texturing semiconductor substrates and the initial start-up of the texturing solutions and methods such that the initial as well as all of the semiconductors textured with the new solutions have the desired average reflectance of below 12% at wavelengths of 360 nm to 1000 nm and etch away 6 μm to 10 μm of silicon per side of the semiconductor. The effected start-up of the texturing solution provides semiconductor wafers with substantially uniform texturing and reduced or no observable flat areas on the textured surface of the semiconductors. Effected start-up prevents sacrificing semiconductor wafers in the initial stages of texturing to prime the texturing composition or bring the composition to its desired operating performance level.

The texturing solutions also include one or more alkaline compounds. Such alkaline compounds include, but are not limited to, alkali metal hydroxides, such as potassium, sodium hydroxide and lithium hydroxide, and quaternary ammonium hydroxides, such as tetramethyl ammonium hydroxide, tetrapropyl ammonium hydroxide, tetrabutyl ammonium hydroxide, tetramethyl-2-hydroxyethyl ammonium hydroxide(choline), trimethyl-3-hydroxypropyl ammonium hydroxide, trimethyl-3-hydroxybutyl ammonium hydroxide, trimethyl-4-hydroxybutyl ammonium hydroxide, tritriethyl-2-hydroxylethyl ammonium hydroxide, tripropyl-2-hydroxyethyl ammonium hydroxide, tributyl-2-hydroxylethyl ammonium hydroxide, dimethylethyl-2-hydroxyethyl ammonium hydroxide, dimethyldi(2-hydroxyethyl ammonium hydroxide, monomethyltri(2-hydroxyethyl) ammonium hydroxide, monomethyltriethyl ammonium hydroxide, monomethyltripropyl ammonium hydroxide, monomethyltributyl ammonium hydroxide, monoethyltrimethyl ammonium hydroxide, monoethyltributyl ammonium hydroxide, dimethyldiethyl ammonium hydroxide and dimethyldibutyl ammonium hydroxide.

Other alkaline components include ammonium hydroxide, alkanolamines such as 2-aminoethanol(monoethanolamine), 1-amino-2-propanol, 1-amino-3-propanol, 2-(2-aminoethoxy)ethanol, 2-(2-aminoethylamino)ethanol. Other suitable alkaline compounds include 3-methoxypropylamine, morpholine, alkane diamines, such as 1,3-pentanedaimine and 2-methyl-1,5-pentanediamine, and guanidine.

Preferably the alkaline compound included in the texturing solution is chosen from one or more hydroxides. More preferably, the alkaline compound is chosen from one or more alkali metal hydroxides, such as sodium and potassium hydroxides. Alkaline compounds are included in the texturing solutions in amounts of 0.5 wt % to 15 wt % of the solution. Preferably, the alkaline compound is included in the texturing solution in amounts of 1 wt % to 10 wt %.

Optionally, the texturing solution may include one or more alkali metal chlorides, such as sodium and potassium chloride and one or more silicates, such as alkali metal silicates, such as the sodium and potassium silicates. Mixture of metal chlorides and metal silicates may be used. Such metal chlorides and metal silicates may be included in the solutions in amounts of 0.01 wt % to 2 wt %, or such as from 0.5 wt % to 1 wt % of the solution.

Optionally, one or more oxygen scavengers may be included in the texturing solutions in sufficient amounts to maintain oxygen content of the solution at 1000 ppb or less. Preferably the oxygen content of the texturing solution during texturing is 1000 ppb to 0 ppb, more preferably the oxygen content of the solution is 500 ppb to 0 ppb. Most preferably the oxygen content is from 200 ppb to 0 ppb. While not being bound by theory, it is believed that the reduced oxygen content assists in inhibiting or preventing formation of flat areas between pyramid structures on the surface of a monocrystalline semiconductor by inhibiting isotropic etching. As mentioned above, the flat areas increase incident light reflectance and reduce the efficiency of the monocrystalline semiconductor.

Oxygen scavengers include, but are not limited to, hydroxyl amine compounds having a formula:

(IV)

wherein $R_5$ and $R_6$ may be the same or different and are hydrogen, substituted or unsubstituted $(C_1-C_{10})$alkyl, substituted or unsubstituted $(C_5-C_{10})$cycloalkyl or substituted or unsubstituted $(C_6-C_{10})$aryl, with the proviso that $R_5$ and $R_6$ are not hydrogen at the same time. Examples of such alkyl groups are methyl, ethyl, propyl, isopropyl, hydroxymethyl, 2-hydroxyethyl, pentyl, t-butyl and octyl. Examples of cycloalkyl groups are cyclopentyl, cyclohexyl, 4-methylcyclohexyl and cyclooctyl. Examples of aryl groups are phenyl, naphthayl, xylyl, 4-hydroxyphenyl and tolyl. Preferred compounds include N-methylhydroxylamine, N-isopropylhydroxylamine, N-cyclohexylhydroxylamine and N,N-diethylhydroxylamine.

Oxygen scavenges also include, but are not limited to, organic acids such as aliphatic, aromatic and amino carboxylic acids and salts thereof. Examples of carboxylic acids are acetic acid, propionic acid, butyric acid, pentanoic acid, 3-methylbutanoic acid, gallic acid, citric acid, lactic acid, ascorbic acid, tartronic acid and 2,4-dihydroxybenzoic acid. Examples of amino carboxylic acids are glycine, dihydroxy ethyl glycine, alanine, valine, leucine, asparagines, glutamine and lysine.

Additional oxygen scavengers include hydrazine, carbohydrazide, erythorbate, methylethylketoxime, hydroquinone, hydroquinone sulfonate, sodium salt, ethoxyquin, methyltetrazone, tetramethylphenylenediamine, DEAE 2-ketogluconate and hydroxyacetone. Preferred compounds are hydroquinone and hydroquinone sulfonate, sodium salt.

In general, oxygen scavengers may be included in the solutions in amounts of 0.001 wt % to 1 wt %. Preferably the oxygen scavengers are included in the solutions in amounts of 0.005 wt % to 0.1 wt % to provide the desired oxygen content of the solution.

In addition to water, the texturing solutions can optionally include one or more organic solvents. Preferably, the texturing solutions include one or more of such organic solvents. Such solvents include aliphatic, alicyclic, aralkyl glycols and cyclic amines. Examples of glycols are ethylene glycol, propylene glycol, 1,3-propanediol, 2,4-dimethyl-2-ethyl-hexane-1,3-diol, 2,2-dimethyl-1,3-propanediol, 2-ethyl-2-butyl-1,3-propanediol, 2-ethyl-2-isobutyl-1,3-propane-diol, 1,3-butanediol, 1,4-butanediol, 1,5-pentanediol, 1,6-hexanediol, 2,2,4-trimethyl-1,6-hexanediol, 1,2-cyclohexanedimethanol, 1,3-cyclohexanedimethanol, 1,4-cyclohexanedimeethanol, 2,2,4,4-tetramethyl-1,3-cyclobutanediol, and p-xylylenediol.

Examples of less preferred organic solvents include cyclic amines such as piperrazine-based compounds, morpholine-based compounds, pyridine-based compounds, piperidine-based compounds, piperidone-based compounds, pyrrolidine-based compounds, pyrrolidone-based compounds and imidazoline-based compounds.

Such organic solvents are included in the solutions in sufficient amounts to solubilize all of the components. Typically such organic solvents are included in amounts of 0.1 wt % to 5 wt %. Preferably solvents which have a flash point of 75° C. or greater is used. Such preferred solvents include, but are not limited to, neopentyl glycol, glycerol, butyl carbitol, 1,5-pentanediol, 1,6-hexanediol, n-methylpyrrolidone (NMP), 1,4-butanediol, 2-pyrrolidone, 1,3-dimethyl-2-imidazolidinone, 4-(2-aminoethyl)morpholine and 1-(2-aminoethyl)piperidine.

The texturing solutions may be applied to a surface of a monocrystalline semiconductor substrate by any suitable method known in the art. The texturing solutions are applied to a surface of the semiconductor substrate at temperatures of 70° C. or higher, typically from 75° C. to 200° C., or such as from 90° C. to 150° C. Typically, the aqueous texturing solutions are applied to a surface of the monocrystalline semiconductor substrate by horizontal or vertical processes. Such methods are well known in the art. Briefly, horizontal methods involve passing the semiconductor substrate on a conveyor system and spraying the solution on the surface of the substrate. In the vertical process the substrate is dipped in the texturing solution. Various conventional apparatus used for such processes are well known in the art. In general, the texturing compositions etch from 6 μm to 10 μm per side of the wafer. Such etching performance is highly desirable. Typically, semiconductor substrates or wafers are cut from a block of silicon using a wire saw. The saw can leave grooves in the semiconductor surface of up to 6 μm to 10 μm. If such saw damage is not substantially removed, electrons can recombine in the area of the saw damage and performance of the electronic device in which the semiconductor is used can drop dramatically.

The texturing solution is applied to a surface of the monocrystalline semiconductor substrate for dwell times of 10 min to 30 min. The hydantoin and hydantoin derivatives provide substantially immediate etching of the silicon surface, thus improving etch efficiency. The semiconductor substrate is then rinsed with water. The texturing method is anisotropic and forms uniform and repeatable pyramid (tetragonal) structures over the entire treated surface of the semiconductor substrate. The pyramid structures are randomly dispersed over the entire treated surface. The pyramid structures may range in height from 1 μm to 10 μm.

The monocrystalline semiconductors textured with the solution reduce reflectance from incident light applied to their textured surfaces. Reflectance of incident light in the 360 nm to 1000 nm wavelength range is less than 12%. Typically reflectance of incident light is from 10% to 11.5%. Reflectance values below 12% are highly desirable because, typically, reflectance values above 12% indicate that pyramid formation during anisotropic etching is not uniform. Reflectance may be measured using conventional reflectometers well known in the art. Accordingly, monocrystalline semiconductors textured by the method using the solutions are suitable for use in devices which convert incident light, such as light from sunlight, lasers, fluorescent light, as well as other sources of light, into electric energy. Such devices include, but are not limited to photovoltaic devices, such as solar cells, optical and electrochemical detectors/sensors, biodetectors/biosensors, catalysts, electrodes, gate electrodes, ohmic contacts, interconnection lines, Schottky barrier diode contacts and optoelectronic components.

Although the texturing method may be used to texture monocrystalline semiconductor substrates for various devices, typically, the texturing method is used in the manufacture of photovoltaic devices, such as solar cells. Typically the semiconductor substrate is in the form of a wafer. Such substrates typically have a p-type base doping. However, texturing may be done on semiconductor wafers prior to any doping or other processing steps. In general, texturing may be done at any convenient time during the manufacture of the photovoltaic device. Typically, the semiconductor substrate is textured before the doping process is complete.

The entire back side of the monocrystalline semiconductor wafer may be metal coated or a portion of the back side may be metal coated, such as to form a grid. Such back side metallization may be provided by a variety of techniques, and may be done prior to the metallization of the front side of the wafer. In one embodiment, a metal coating is applied to the back side in the form of an electrically conductive paste, such as a silver-containing paste, an aluminum-containing paste or a silver and aluminum-containing paste; however, other suitable pastes known in the art also may be used. Such conductive pastes typically include conductive particles embedded in a glass matrix and an organic binder. Conductive pastes may be applied to the wafer by a variety of techniques, such as screen printing. After the paste is applied, it is fired to remove the organic binder. When a conductive paste containing aluminum is used, the aluminum partially diffuses into the back side of the wafer, or if used in a paste also containing silver, may alloy with the silver. Use of such aluminum-containing paste may improve the resistive contact and provide a "p+"-doped region. Heavily doped "p+"-type regions by previous application of aluminum or boron with subsequent interdiffusion may also be produced. Optionally, a seed layer may be deposited on the back side of the wafer and a metal coating may be deposited on the seed layer by electroless or electrolytic plating.

To produce the semiconductor junction, phosphorus diffusion or ion implantation takes place on the front side of the wafer to produce an n-doped (n+ or n++) region and provides the wafer with a PN junction. The n-doped region may be referred to as the emitter layer. Typically the monocrystalline semiconductor wafer is of silicon.

The front side or emitter layer of the wafer is subjected to anisotropic texturing in order to impart to the surface an improved light incidence geometry which reduces reflections. The texturing is applied to the emitter layer for 10 min. to 30 min, typically from 10 min. to 15 min. to form uniform and randomly dispersed pyramid structures on the emitter layer. The texturing solutions have surface tensions of 72 dynes/cm$^2$ or less, preferably 40 dynes/cm$^2$ or less. More preferably the surface tension is 20-40 dynes/cm$^2$. After a dwell time of 10 min. to 30 min., the wafer is rinsed with water to remove the texturing solution.

An anti-reflective layer is added to the front side or emitter layer of the wafer. In addition the anti-reflective layer may serve as a passivation layer. Suitable anti-reflective layers include, without limitation, silicon oxide layers such as $SiO_x$, silicon nitride layers such as $Si_3N_4$, a combination of silicon oxide and silicon nitride layers, and combinations of a silicon oxide layer, a silicon nitride layer with a titanium oxide layer such as $TiO_x$. In the foregoing formulae, x is an integer representing the number of oxygen atoms. Such anti-reflective layers may be deposited by a number of techniques, such as by various vapor deposition methods, for example, chemical vapor deposition and physical vapor deposition.

The front side of a wafer contains a metallized pattern. For example, the front side of a wafer may be composed of current collecting lines and current busbars. Current collecting lines are typically transverse to the busbars and typically have a relatively fine-structure (i.e. dimensions) relative to current busbars.

The pattern reaches through the antireflective layer to expose the surface of the semiconductor body of the wafer. Alternatively trenches may be formed in the openings to create a selective emitter. These trenches may be regions of high doping. A variety of processes may be used to form the pattern, such as, but not limited to, laser ablation, mechanical means, and lithographic processes, all of which are well known in the art. Such mechanical means include sawing and scratching. Typical photolithographic processes include disposing an imageable material on the surface of the wafer, patterning the imageable material to form openings in the anti-reflective layer, transferring the pattern to the wafer, depositing a nickel layer in the openings and removing the imageable material. In one embodiment, the imageable material is removed before the step of depositing a metal layer in the openings. In another embodiment, the imageable material is removed after the step of depositing a metal layer in the openings. When the imageable material is present during the metal deposition step, such imageable material typically avoids any dyes, such as contrast dyes, that absorb in the wavelength of radiation used during the nickel deposition step. Imageable material present during the plating step typically contains a dye which has a minimum light transmittance of 40-60%.

The imageable material may be removed using any suitable polymer remover. Such removers may be alkaline, acidic or essentially neutral and are well known in the art.

In one embodiment, the front side of the wafer may be metallized using a conductive paste, which may be the same as or different from any conductive paste used on the rear side of the wafer. Any conductive paste used to metallize the front side of a wafer typically does not contain aluminum. The temperature used in the firing of the paste depends on the particular paste used, the thickness of any antireflective layer used, among other factors. The choice of such temperature is well within the ability of those skilled in the art. Also, it is appreciated by those skilled in the art that the firing process may be performed in an oxygen-containing atmosphere, an inert atmosphere, a reducing atmosphere, or a combination of any of these. For example, the firing may be performed at a first temperature in an atmosphere containing little oxygen and then at a second temperature under an inert atmosphere or under a reducing atmosphere, where the second temperature is higher than the first temperature.

Following the firing process, the wafer may optionally be contacted with a buffered acid solution, such as a buffered hydrofluoric acid solution, to remove any oxide produced during the firing procedure. Such contact may be by spraying the solution on the wafer or by dipping the wafer into such solution or by any other suitable means.

After the front side pattern and rear side of the wafer are metallized using conductive paste, a layer of metal is then deposited on the front side conductive pattern. Such layer of metal may be any suitably conductive metal such as gold, silver or copper, and is typically silver. Such metals may be deposited by methods known in the art. In one embodiment, the deposited metal layer is composed of the same metal used in the conductive paste. For example, a silver layer is deposited on a silver-containing conductive paste.

Silver may be deposited by light induced plating (LIP) or conventional silver electroplating methods well known in the art. When LIP is used, the rear side of the semiconductor wafer is connected to a source of external current (rectifier). A silver anode placed in the silver plating composition is connected to the rectifier such that a completed circuit is formed between the components. Typical current densities are from 0.1 A/dm$^2$ to 5 A/dm$^2$. The total current requirement is dependent upon the particular size of the wafer used. Additionally, the silver anode provides a ready source of silver ions to replenish the silver plating composition with silver ions without the need to use an external source. A light source is positioned to illuminate the semiconductor wafer with light energy. The light source can be, for example, a fluorescent or LED lamp which provides energy within the wavelengths to which the semiconductor wafer is photovoltaically sensitive. A variety of other light sources may be used, such as, but not limited to, incandescent lamps such as a 75 watt and 250 watt lamps, mercury lamps, halogen lamps and a 150 watt IR lamp. Examples of commercially useful silver plating compositions are available as ENLIGHT™ Silver Plate 600 and 620 from Rohm and Haas Electronic Materials, LLC Marlborough, Mass.

The plating cell is of such a material as to be chemically inert with respect to the silver plating composition and has a minimum light transmittance of 40-60%. Alternatively, the wafer can be positioned horizontally in the plating cell and illuminated from above the silver plating composition, in which case the plating cell need not have at least the minimum light transmittance.

In another embodiment a metal seed layer may be deposited on the front side conductive pattern instead of a metal paste. Typically the metal seed layer is nickel. The nickel seed layer may be deposited by any conventional nickel deposition method known in the art. Typically, the nickel seed layer is deposited by light assisted nickel deposition. If the source of the nickel is an electroless nickel composition, plating is done without application of external current. If the source of the nickel is from an electrolytic nickel composition, a rear side potential (rectifier) is applied to the semiconductor wafer substrate. The light may be continuous or pulsed. Prior to depositing nickel, surface oxides are typically removed from the conductive pattern using a solution of 1% hydrofluoric acid.

Light which may be used in the plating process includes, but is not limited to, visible light, IR, UV and X-rays. Light sources include, but are not limited to, incandescent lamps, LED lights (light emitting diodes), infrared lamps, fluorescent lamps, halogen lamps and lasers. In general the amount of light applied to the semiconductor may be 8000 lx to 20,000 lx.

Typically, nickel is deposited through the openings in the anti-reflective layer and onto the exposed textured surface of the semiconductor wafer using an electroless nickel plating composition. Examples of commercially available electroless nickel compositions include DURAPOSIT™ SMT 88 Electroless Nickel and NIPOSIT™ PM 980 and PM 988 Electroless Nickel. All are available from Rohm and Haas Electronic Materials, LLC, Marlborough, Mass., U.S.A.

Alternatively, electrolytic nickel compositions may be used. When an electrolytic composition is used, an applied rear side potential (rectifier) is used in addition to light to deposit the nickel. Typical current densities are from 0.1 A/dm$^2$ to 2 A/dm$^2$. The particular current requirement is dependent upon the particular size of the wafer used. The electroplating processes used are conventional. Suitable electrolytic nickel plating baths are commercially available as well as many which are disclosed in the literature. Examples of commercially available electrolytic nickel baths are the NICKEL GLEAM™ Electrolytic Nickel products obtainable from Rohm and Haas Electronic Materials, LLC.

By illuminating the front of the semiconductor wafer with light energy, plating occurs on the front. The impinging light energy generates a current in the semiconductor. The rate of plating on the front is controllable by adjusting the light intensity, bath temperature, reducing agent activity, starting wafer conditions, doping level as well as other parameters which are known to workers in the art. If the plating bath is an electrolytic bath the rate of plating may also be adjusted by the rectifier. A nickel layer of 20 nm to 300 nm thickness is typically desired, with the exact thickness depending on various factors such as on the application, size, pattern and geometry.

After the nickel is deposited through the openings and adjacent to the exposed surface of the semiconductor wafer substrate, silver is then deposited adjacent to the nickel. Conventional electroplating silver compositions may be used. The silver compositions may be cyanide containing silver compositions or cyanide-free silver compositions.

Silver may deposited on the nickel by light induced plating (LIP) or conventional silver electroplating methods well known in the art. The procedure of LIP plating is similar to that for plating the silver paste described above. A silver layer of 1 μm to 30 μm thickness is typically desired, with the exact thickness depending on various factors such as on the application, size, pattern and geometry.

After the silver metal is deposited onto and adjacent the nickel, the semiconductor is then sintered to form nickel silicide. Sintering is done with the silver deposited onto the nickel surface to improve adhesion between the silver and nickel. The improved bonding between the nickel and the silicon reduces the probability of adhesion failure between the nickel silicide and the silver. Further, silver is not incorporated into the silicide by the sintering temperatures, thus nickel silicide is formed with the silver protecting the nickel from oxidation during sintering. A furnace providing a wafer peak temperature of 380° C. to 550° C. may be used. Typically, peak temperature times range from 2 seconds to 20 seconds. An example of a suitable furnace is a lamp based furnace (IR).

Since the silver layer protects the nickel from oxidation during sintering, sintering may be done in oxygen containing environments as well as inert gas atmosphere or vacuum. In general, sintering is done for 3 min. to 10 min. Line speeds at which the semiconductor passes through the furnace may vary depending on the furnace used. Minor experimentation may be done to determine the appropriate line speed. Typically, the line speed is from 330 cm/minute to 430 cm/minute.

The methods and compositions are used to anisotropically texture monocrystalline semiconductors for photovoltaic devices, including semiconductors in the manufacture of solar cells. The addition of one or more of hydantoin and hydantoin derivatives in combination with one or more alkoxylated glycols inhibit or reduce formation of flat areas between pyramid structures on the textured monocrystalline semiconductors to increase incident light absorption and improve the efficiency of the devices. In addition, the hydantoin compounds improve the efficiency of the texturing method.

The following examples are included to illustrate the invention but are not intended to limit its scope.

Example 1

Two doped monocrystalline silicon semiconductor wafers (obtained from SolarGiga) having n+ doped zones on the front side or emitter layer and a pn-junction below the emitter layer were textured with one of the two texturing solutions shown in Table 1.

TABLE 1

| Component | Solution 1 | Solution 2 |
|---|---|---|
| Tripropylene glycol[1] | 2 wt % | 2 wt % |
| Potassium hydroxide | 6 wt % (25 g/L) | 6 wt % (25 g/L) |
| 1,4-butanediol[2] | 2 wt % | 2 wt % |
| N-isopropylhydroxylamine[3] | 0.1 wt % | 0.1 wt % |

TABLE 1-continued

| Component | Solution 1 | Solution 2 |
|---|---|---|
| Hydantoin[4] | 0 | 0.05 wt % |
| Water | Balance | Balance |

[1] weight average molecular weight = 192 g/mole, flash point = 140.5° C., Boiling point = 268° C.;
[2] Flash point = 121° C.;
[3] Hydroguard™ I-15 (available from The Dow Chemical Company, Midland, MI);
[4] melting point = 221-223° C. (Decomposes).

Each wafer was immersed in one of the two texturing solutions for 10 minutes. The solutions were kept at 80° C. and the pH of the solutions was at 13 measured with a conventional laboratory pH meter.

Figure 1:
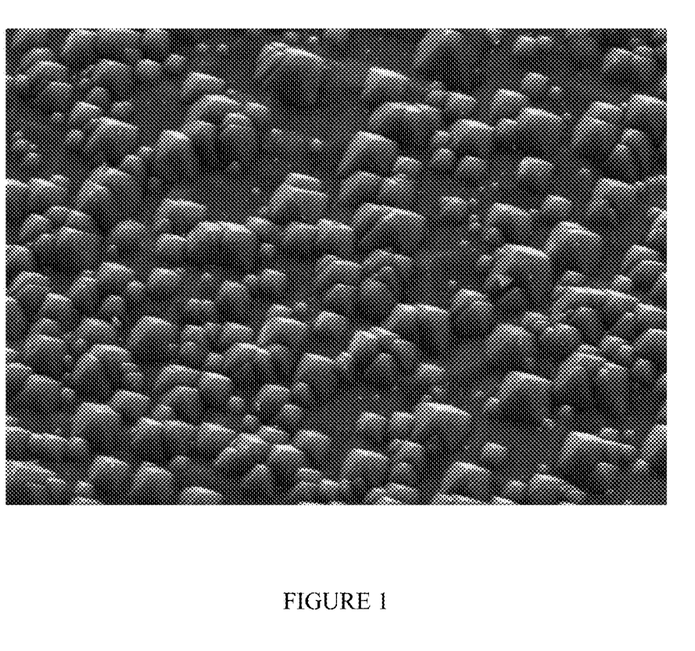
FIG. 1 is a 1000×SEM taken at a 30° angle of a monocrystalline silicon semiconductor wafer textured in an alkaline bath without a hydantoin compound.
Figure 2:
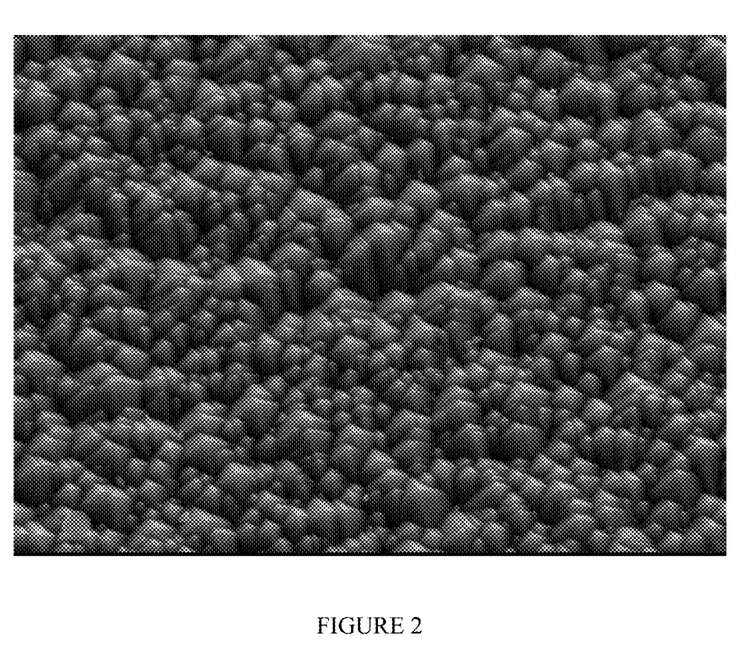
FIG. 2 is a 1000×SEM taken at a 30° angle of a monocrystalline silicon semiconductor wafer textured in an alkaline bath containing hydantoin.

FIG. 1 is a SEM of the wafer textured with solution 1 taken with an AMRAY 1510 Field Emission scanning electron microscope taken at an angle of 30 degrees. FIG. 1 shows numerous flat areas on the emitter layer of the wafer among the pyramid structures. Such flat areas may have been caused by isotropic etching of the wafer. In contrast, FIG. 2 is a SEM taken at an angle of 30 degrees of the wafer textured with solution 2 which included hydantoin. No flat areas were observed only pyramid structures. The presence of pyramid structures and lack of flat areas indicated that only anisotropic texturing occurred on the emitter layer of the wafer.

Examples 2-5

Controls

Four aqueous based texturing solutions were made as shown in Table 2 below. Four monocrystalline silicon semiconductor wafers (obtained from SolarGiga) having n+ doped zones on the front side or emitter layer and a pn-junction below the emitter layer were weighed using a conventional laboratory balance. Each wafer was then immersed in one of the four texturing solutions for 30 minutes at 75° C. The pH of the texturing solutions was 13. The wafers were then removed from their respective texturing solutions, rinsed with water and air dried. Each wafer was then weighed and the amount of silicon etched per side was determined as shown in Table 2 below.

Reflectance of the textured surface was determined using a MacBeth Coloreye Reflectometer 7000 at the wavelength of 600 nm The source of the incident light was a pulsed xenon bulb. An average of 6 reflectance readings was taken across the surface of each wafer. The average reflectance is shown in Table 2.

TABLE 2

| ADDITIVE (Examples 2-5) | SODIUM HYDROXIDE (g/L) | TPG (wt %) | TIME (minutes) | TEMPERATURE (° C.) | ETCH/SIDE (µm) | REFLECTANCE (% at 600 nm) |
|---|---|---|---|---|---|---|
| Tripropylene glycol (TPG) | 17.85 | 0.6 | 30 | 75 | 13.56 | 13.98 |
| Tripropylene glycol | 17.85 | 1.2 | 30 | 75 | 9.66 | 14.89 |
| Tripropylene glycol | 17.85 | 1.2 | 30 | 75 | 10.24 | 16.33 |
| Tripropylene glycol | 17.85 | 2.4 | 30 | 75 | 8.24 | 21.12 |

Although wafers textured with the solutions of Examples 3 and 5 had etch values of below 10 µm/side, the % reflectance of the wafers had values exceeding 12%.

Examples 6-7

Controls

Two aqueous based texturing solutions were made as shown in Table 3 below. Two monocrystalline silicon semiconductor wafers (obtained from SolarGiga) having n+ doped zones on the front side or emitter layer and a pn-junctions below the emitter layer were weighed using a conventional laboratory balance. Each wafer was then immersed in one of the two texturing solutions for 30 minutes at 75° C. The wafers were then removed from their respective texturing solutions, rinsed with water and air dried. Each wafer was then weighed and the amount of silicon etched per side was determined as shown in Table 3 below.

Reflectance of the textured surface was determined using the MacBeth Coloreye Reflectometer 7000 at the wavelength of 600 nm. An average of 6 reflectance readings was taken across the surface of each wafer. The average reflectance is shown in Table 3.

TABLE 3

| ADDITIVE (Examples 6-7) | SODIUM HYDROXIDE (g/L) | ADDITIVE (wt %) | TIME (minutes) | TEMPERATURE (° C.) | ETCH/SIDE (μm) | REFLECTANCE (% at 600 nm) |
|---|---|---|---|---|---|---|
| 1,4-butanediol | 17.85 | 1.2 | 30 | 75 | 11.12 | 16.23 |
| 1,4-butanediol | 17.85 | 1.2 | 30 | 75 | 11.86 | 16.15 |

Both wafers textured with the solutions of Examples 6 and 7 had etchings of greater than 10 μm and reflectance values exceeding 12%.

Examples 8-9

Controls

The process described in Examples 6-7 above was repeated except that the additive to the texturing solutions was isopropyl alcohol (IPA). The results are shown in Table 4.

TABLE 4

| ADDITIVE (Examples 8-9) | SODIUM HYDROXIDE (g/L) | IPA (wt %) | TIME (minutes) | TEMPERATURE (° C.) | ETCH/SIDE (μm) | REFLECTANCE (% at 600 nm) |
|---|---|---|---|---|---|---|
| Isopropyl alcohol | 17.85 | 4 | 30 | 75 | 14.05 | 12.28 |
| Isopropyl alcohol | 17.85 | 6 | 30 | 75 | 11.19 | 17.25 |

Both wafers textured with the solutions of Examples 8 and 9 had etchings of greater than 10 μm and reflectance values exceeding 12%.

Examples 10-20

Working Examples

Eleven aqueous based texturing solutions containing hydantoin, dimethylhydantoin or 2-thiohydantoin, 17.85 g/L sodium hydroxide and 1.2 wt % tripropylene glycol were made. Eleven monocrystalline silicon semiconductor wafers (obtained from SolarGiga) having n+ doped zones on the front side or emitter layer and a pn-junction below the emitter layer were weighed using a conventional laboratory balance. Each wafer was then immersed in one of the eleven texturing solutions for 30 minutes at 75° C. The pH of the solutions ranged from 13-14. The wafers were then removed from their respective texturing solutions, rinsed with water and air dried. Each wafer was then weighed and the amount of silicon etched per side was determined as shown in Table 5 below.

Reflectance of the textured surface was determined using the MacBeth Coloreye Reflectometer 7000 at the wavelength of 600 nm. An average of 6 reflectance readings was taken across the surface of each wafer. The average reflectance is shown in Table 5.

TABLE 5

| ADDITIVE (Examples 10-20) | ADDITIVE (wt %) | ETCH/SIDE (μm) | REFLECTANCE (% at 600 nm) |
|---|---|---|---|
| Hydantoin | 0.05 | 7.82 | 11.19 |
| Dimethylhydantoin | 0.05 | 8.31 | 11.46 |
| Dimethylhydantoin | 0.3 | 8.55 | 11.44 |
| 2-thiohydantoin | 0.01 | 6.51 | 11.13 |
| 2-thiohydantoin | 0.05 | 7.09 | 11.27 |
| 2-thiohydantoin | 0.05 | 6.79 | 11.15 |
| 2-thiohydantoin | 0.1 | 6.68 | 11.14 |
| 2-thiohydantoin | 0.1 | 6.65 | 10.73 |
| 2-thiohydantoin | 0.3 | 7.00 | 11.36 |
| 2-thiohydantoin | 0.3 | 7.08 | 11.53 |
| 2-thiohydantoin | 0.5 | 7.01 | 11.48 |

The wafers textured with the aqueous alkaline texturing solutions which included hydantoin, dimethylhydantoin or 2-thiohydantoin all had etching values below 10 μm and reflectance values below 12%. Wafers textured with the hydantoin and hydantoin derivative texturing solutions showed improvement in both etching as well as in incident light reflectance compared to the controls of Examples 2-9.

Examples 21-32

Comparatives

The process described in Examples 10-20 was repeated except the additives to the texturing solutions were heterocyclic compounds shown in Table 6 below. Each texturing solution also included 17.85 g/L of sodium hydroxide and 1.2 wt % tripropylene glycol. Etching time was 30 minutes and the temperature of the texturing solutions was 75° C. The pH of each solution ranged from 13-14.

TABLE 6

| ADDITIVE (Examples 21-32) | ADDITIVE (wt %) | ETCH/SIDE (μm) | REFLECTANCE (% at 600 nm) |
|---|---|---|---|
| sodium isoascorbate monohydrate | 1.2 | 9.29 | 15.67 |

TABLE 6-continued

| ADDITIVE (Examples 21-32) | ADDITIVE (wt %) | ETCH/SIDE (μm) | REFLECTANCE (% at 600 nm) |
|---|---|---|---|
| 2-pyrrolidone | 1.2 | 10.31 | 15.57 |
| 1-(2-hydroxy)-2-pyrrolidone | 1.2 | 11.14 | 16.16 |
| d (−) isoascorbic acid | 1.2 | 7.29 | 16.05 |
| Histidine | 0.3 | 9.78 | 15.03 |
| Niacin | 1.2 | 9.54 | 21.13 |
| Nicotinamide | 1.2 | 9.93 | 19.95 |
| Adenine | 0.3 | 6.93 | 15.54 |
| Quinoxaline | 0.3 | 10.08 | 22.35 |
| Capralactone | 1.2 | 9.49 | 19.62 |
| Capralactam | 1.2 | 9.50 | 21.28 |
| Pyridizine | 0.3 | 5.70 | 16.84 |

With the exception of comparative Examples 22, 23 and 29, the wafers textured with the solutions containing the heterocyclic compounds of Table 6 had etching values of less than 10 μm. However, the reflectance values for all of the wafers etched with the texturing solutions exceeded 12%. The wafers textured with the solutions containing hydantoin and hydantoin derivatives of Examples 10-20 showed improved reflectance values in contrast to the wafers etched with the comparative examples.

Examples 33-39

Comparatives

The process described in Examples 10-20 was repeated except the additives to the texturing solutions were heterocyclic compounds shown in Table 7 below. Each texturing solution also included 17.85 g/L of sodium hydroxide and 1.2 wt % tripropylene glycol, except Example 34 which included tripropylene glycol at 0.3 wt %. Etching time was 30 minutes and the temperature of the texturing solutions was 75° C. The pH of each solution ranged from 13-14.

TABLE 7

| ADDITIVE (Examples 33-39) | ADDITIVE (wt %) | ETCH/SIDE (μm) | REFLECTANCE (% at 600 nm) |
|---|---|---|---|
| 1,3-dimethy-2-imidazolidinone | 0.3 | 9.29 | 15.69 |
| 1,3-dimethy-2-imidazolidinone | 1.2 | 10.17 | 12.73 |
| 1,3-dimethy-2-imidazolidinone | 1.2 | 7.99 | 13.68 |
| 4-(2-aminoethyl)morpholine | 0.1 | 11.31 | 16.98 |
| 4-(2-aminoethyl)morpholine | 0.3 | 9.85 | 13.45 |
| 4-(2-aminoethyl)morpholine | 1.2 | 10.92 | 15 |
| 1-(2-aminoethyl)-piperizine | 1.2 | 13.04 | 15.97 |

Wafers textured with the solutions of comparative Examples 33, 35 and 37 had etch values below 10 μm; however their reflectance values still exceeded 12%. The wafers etched with solutions of comparative Examples 34, 36, 38 and 39 had high etch values exceeding 10 μm as well as high reflectance values above 12%.

Examples 40-52

Comparative

The process described in Examples 10-20 was repeated except the additives to the texturing solutions were compounds shown in Table 8 below. Comparative Examples 40, 41, 42 and 43 also included 11 g/L, 14.5 g/L, 21.5 g/L and 25 g/L sodium hydroxide, respectively. The remainder of the solutions included 17.85 g/L of sodium hydroxide. Each solution also included 1.2 wt % tripropylene glycol except comparative Examples 44 and 45 which included tripropylene glycol in amounts of 0.6 wt % and 0.9 wt %, respectively. Etching time was 30 minutes and the temperature of the texturing solutions was 75° C. The pH of each solution ranged from 13-14.

TABLE 8

| ADDITIVE (Examples 40-52) | ADDITIVE (wt %) | ETCH/SIDE (μm) | REFLECTANCE (% at 600 nm) |
|---|---|---|---|
| 1-(2-hydroxyethyl) piperazine | 0.3 | 9.24 | 25.27 |
| 1-(2-hydroxyethyl) piperazine | 0.3 | 11.01 | 21.16 |
| 1-(2-hydroxyethyl) piperazine | 0.3 | 12.29 | 12.69 |
| 1-(2-hydroxyethyl) piperazine | 0.3 | 14.14 | 14.07 |
| 1-(2-hydroxyethyl) piperazine | 0.3 | 15.00 | 13.47 |
| 1-(2-hydroxyethyl) piperazine | 0.3 | 12.23 | 12.64 |
| 1-(2-hydroxyethyl) piperazine | 0.05 | 11.61 | 13.37 |
| 1-(2-hydroxyethyl) piperazine | 0.1 | 12.37 | 13.18 |
| 1-(2-hydroxyethyl) piperazine | 0.3 | 9.06 | 11.6 |
| 1-(2-hydroxyethyl) piperazine | 0.3 | 9.19 | 12.54 |
| 1-(2-hydroxyethyl) piperazine | 0.3 | 11.45 | 13.64 |
| 1-(2-hydroxyethyl) piperazine | 0.3 | 10.40 | 11.78 |
| 1-(2-hydroxyethyl) piperazine | 0.5 | 11.97 | 13 |

Only the wafer textured with the solution of comparative Example 48 had both an etch value below 10 μm and a reflectance below 12%. Overall the wafers etched with the solutions of 1-(2-hydroxyethyl) piperazine were inferior to the wafers etched with the hydantoin and hydantoin derivatives of Examples 10-20.

Examples 53-66

Comparatives

The process described in Examples 10-20 was repeated except the additives to the texturing solutions were compounds shown in Table 9 below. Each solution also included 17.85 g/L of sodium hydroxide and 1.2 wt % tripropylene glycol. Etching time was 30 minutes and the temperature of the texturing solutions was 75° C. The pH of each solution ranged from 13-14.

TABLE 9

| ADDITIVE (Examples 53-66) | ADDITIVE (wt %) | ETCH/SIDE (μm) | REFLECTANCE (% at 600 nm) |
|---|---|---|---|
| Pyrazine | 0.05 | 7.99 | 11.91 |
| Pyrazine | 0.3 | 10.72 | 12.23 |
| Pyrazine | 0.3 | 11.10 | 13.01 |
| Pyrazine | 0.3 | 8.58 | 13.13 |

TABLE 9-continued

| ADDITIVE (Examples 53-66) | ADDITIVE (wt %) | ETCH/SIDE (μm) | REFLECTANCE (% at 600 nm) |
|---|---|---|---|
| Benzotriazole | 0.3 | 7.73 | 14.28 |
| Benzotriazole-5-carboxylic acid | 0.05 | 10.48 | 16.96 |
| Benzotriazole-5-carboxylic acid | 0.3 | 6.90 | 16.41 |
| Benzotriazole-2-carobxylic acid | 0.05 | 3.24 | 21.58 |
| Benzotriazole-2-carobxylic acid | 0.3 | 1.90 | 21.3 |
| 3-amino-1,2,4-triazine | 0.0001 | 10.05 | 12.41 |
| 3-amino-1,2,4-triazine | 0.001 | 10.22 | 14.72 |
| 3-amino-1,2,4-triazine | 0.01 | 13.10 | 29.89 |
| 3-amino-1,2,4-triazine | 0.05 | 15.60 | 28.06 |
| 3-amino-1,2,4-triazine | 0.3 | 17.57 | 32.22 |

Comparative Example 53 which included 0.05 wt % pyrazine had an etch value below 10 μm and a % reflectance below 12; however Examples 54-56 which included 0.3 wt % pyrazine had etch values exceeding 10 μm and reflectance values above 12%. While Examples 57 and 59 had etch values below 10 μm but above 6 μm, their reflectance values exceeded 12%. Examples 60 and 61 had etch values below 6 μm and reflectance values exceeding 12%. Examples 10-20 which included the hydantoin and hydantoin derivatives showed overall better results since the etch values were below 10 μm and above 6 μm and all of their reflectance values were below 12%.

Example 67-72

Comparatives

The process described in Examples 10-20 was repeated except the additives to the texturing solutions were compounds shown in Table 10 below. Each solution also included 17.85 g/L of sodium hydroxide and 1.2 wt % tripropylene glycol. Etching time was 30 minutes and the temperature of the texturing solutions was 75° C. The pH of each solution ranged from 13-14.

TABLE 10

| ADDITIVE (Examples 67-72) | ADDITIVE (wt %) | ETCH/SIDE (μm) | REFLECTANCE (% at 600 nm) |
|---|---|---|---|
| 2-mercaptobenzoxazole | 0.05 | 2.05 | 15.74 |
| 2-mercaptobenzoxazole | 0.05 | 6.81 | 15.09 |
| 2-mercaptobenzoxazole | 0.3 | 5.13 | 18.26 |
| 5-mercapto-1-tetrazole | 0.3 | 9.23 | 16.58 |
| 5-mercapto-1-tetrazole | 0.05 | 8.03 | 12.21 |
| 5-mercapto-1-tetrazole | 0.3 | 7.68 | 14.68 |

Although the etch values for comparative Examples 67-72 are all below 10 μm, all of the reflectance values exceed 12%.

What is claimed is:

1. A method comprising:
   a) providing a monocrystalline semiconductor substrate;
   b) providing a composition comprising one or more compounds chosen from hydantoin and hydantoin derivatives, one or more alkoxylated glycols, one or more oxygen scavengers and one or more alkaline compounds; and
   c) contacting the monocrystalline semiconductor substrate with the composition to anisotropically texture the monocrystalline semiconductor substrate.

2. The method of claim 1, wherein the one or more of hydantoin and hydantoin derivatives range from 0.005 wt % to 0.09 wt % of the composition.

3. The method of claim 1, wherein the one or more alkoxylated glycols have molecular weights of 100 g/mole or greater.

4. The method of claim 1, wherein the solution further comprises one or more organic solvents.

* * * * *